(12) United States Patent
Pomeroy et al.

(10) Patent No.: US 7,841,998 B2
(45) Date of Patent: Nov. 30, 2010

(54) FIXATOR OR SPLINT

(76) Inventors: Linda Pomeroy, 19. Luralda Wharf, 40 Saunders Ness Road, Isle of Dogs, London (GB) E14 3BY; Ali Bajwa, 51 Woodvale, Coulby Newham, Middlesborough (GB) TS8 0SJ ( * ) Notice: Subject to any disclaimer, the term of this patent is extended or adjusted under 35 U.S.C. 154(b) by 0 days.

(21) Appl. No.: 11/914,191

(22) PCT Filed: May 12, 2006

(86) PCT No.: PCT/GB2006/050102
§ 371 (c)(1),
(2), (4) Date: Feb. 13, 2008

(87) PCT Pub. No.: WO2006/120482
PCT Pub. Date: Nov. 16, 2006

(65) Prior Publication Data
US 2008/0200855 A1    Aug. 21, 2008

(51) Int. Cl.
  *A61F 5/00*    (2006.01)
  *A61B 17/00*   (2006.01)
(52) U.S. Cl. .................. 602/16; 602/5; 606/54
(58) Field of Classification Search .............. 602/5, 602/16, 20, 54, 12, 19, 21, 23, 26, 27; 606/54, 606/55, 53, 260, 266, 277, 57, 90, 105
See application file for complete search history.

(56) References Cited

U.S. PATENT DOCUMENTS

| | | | |
|---|---|---|---|
| 1,789,060 A * | 1/1931 | Weisenbach ............. 606/54 |
| 4,180,870 A * | 1/1980 | Radulovic et al. .......... 623/26 |
| 4,497,315 A | 2/1985 | Fettweis et al. |
| 4,538,600 A | 9/1985 | Hepburn et al. |
| 4,677,971 A * | 7/1987 | Lindemann ............ 602/21 |
| 4,834,057 A * | 5/1989 | McLeod, Jr. ............. 600/595 |
| 4,977,890 A | 12/1990 | Mann |
| 5,002,044 A * | 3/1991 | Carter ................... 602/16 |
| 5,316,547 A * | 5/1994 | Gildersleeve ............. 602/26 |
| 5,385,536 A | 1/1995 | Burkhead et al. |
| 5,421,810 A * | 6/1995 | Davis et al. ............. 602/16 |

(Continued)

FOREIGN PATENT DOCUMENTS

DE    82 161 C    7/1895

(Continued)

OTHER PUBLICATIONS

International Search Report for corresponding PCT/GB2006/050102 completed Sep. 8, 2006 by Jean-Charles Assion of the EPO.

(Continued)

*Primary Examiner*—Patricia M Bianco
*Assistant Examiner*—Victoria Hicks (57) ABSTRACT

The present invention relates to a non-invasive external fixator particularly suitable for fracture fixation. In particular, the fixator of the invention includes proximal and distal portions for mounting on a limb either side of a fracture. Each of the proximal and distal portions includes a rigid member. An articulation member connects the proximal and distal portions. The articulation member includes a universal joint for allowing relative movement between the proximal and distal portions, wherein the articulation member connects the rigid members.

22 Claims, 5 Drawing Sheets

U.S. PATENT DOCUMENTS

| | | | |
|---|---|---|---|
| 5,437,619 A * | 8/1995 | Malewicz et al. | 602/20 |
| 5,514,081 A | 5/1996 | Mann et al. | |
| 5,545,162 A | 8/1996 | Huebner et al. | |
| 5,683,353 A * | 11/1997 | Hamersly | 602/16 |
| 5,707,370 A | 1/1998 | Berki et al. | |
| 5,846,245 A * | 12/1998 | McCarthy et al. | 606/105 |
| 5,916,184 A * | 6/1999 | McKeel | 602/6 |
| 6,019,769 A | 2/2000 | McCarthy et al. | |
| 6,179,799 B1 | 1/2001 | Doran | |
| 6,589,195 B1 * | 7/2003 | Schwenn et al. | 602/23 |
| 6,676,619 B2 * | 1/2004 | Arden | 602/8 |
| 7,416,537 B1 * | 8/2008 | Stark et al. | 602/16 |
| 7,476,207 B2 * | 1/2009 | Porrata et al. | 602/13 |
| 2002/0035342 A1 | 3/2002 | Williams | |

FOREIGN PATENT DOCUMENTS

| | | |
|---|---|---|
| EP | 1 382 317 A1 | 1/2004 |
| FR | 2 609 887 | 7/1988 |
| WO | WO 94/23662 A | 10/1994 |

OTHER PUBLICATIONS

British Search Report for corresponding GB0509613.6; Claims searched 1-24; Date of Search: Apr. 13, 2006.

* cited by examiner

FIXATOR OR SPLINT

RELATED APPLICATIONS

The present invention claims priority from PCT Patent Application No. PCT/GB2006/050102, filed May 12, 2006; which claims priority of United Kingdom Patent Application No. GB0509613.6 filed May 12, 2005.

FIELD OF THE INVENTION

The present invention relates to a non-invasive external fixator particularly suitable for fracture fixation. Particular embodiments of the invention relate to an external fixator which allows for movement in a joint adjacent a fracture site; while certain embodiments relate to a fixator useful in movement, distraction and/or reduction of a fracture.

BACKGROUND TO THE INVENTION

When a bone is fractured, it is often necessary to hold the fragments of the bone together to allow for correct healing. If this is not done, problems such as misalignment or poor healing can occur.

A conventional means for fixing fracture fragments is an external fixator, which typically takes the form of a steel or other material rod spanning across the fracture which is fixed to the bone fragments using pins. The rod is located outside the body, while the pins penetrate the skin and are fixed in the bone. This invasive technique involves surgery, and as such there is a risk of infection of the soft tissue or bone, and further there is a risk of complications arising from the surgery.

A further disadvantage of conventional external fixators is where the fixator spans a joint, such as the wrist or ankle. The steel or other material rod may not be articulated, thereby preventing movement of the joint.

Articulated fixators are known, but these have disadvantages as well. Alignment of the articulation with the joint can be difficult if not impossible, due to articulation of the fixator not being in the plane of the joint line axis. Known devices do not allow movement in the joint's plane of motion. For example, the position of the articulation of the fixator is dependent on the position of the pins drilled in the bone which can only be drilled in a limited number of positions. Furthermore, known articulated fixators also have the disadvantage that if the fractured joints are moved in fracture situation, this will disturb the fracture position. In particular, known devices allow for multidirectional movement, including rotation, thereby allowing the fracture position to slip.

U.S. Pat. No. 4,677,971 discloses a wrist splint for the treatment of soft tissue injuries, as a splint after surgery or in fracture treatment of small bones of the wrist (carpal bones). However, the device does not have rigid members connected by an articulation piece according to the present invention. Furthermore, as with other known devices, the device in U.S. Pat. No. 4,677,971 is not suitable for treating long bone fractures because the articulation piece is not at the fracture site or joint level and does not allow movement in the joint plane.

In certain locations, such as for a fracture of the radial bone, the patient's thumb may prevent suitable alignment of the steel rod and the articulation. This problem has been addressed to a certain extent with ring external fixators, such as Ilazarov. However, such fixators necessitate a number of invasive pin placements and lead to a very big and cumbersome fixator.

It is an object of the present invention to obviate or alleviate these and other disadvantages of conventional fixators. It is a further object of the invention to provide a non-invasive external fixator, which permits movement of a joint near the fracture site and also allows for fracture reduction and aids fracture manipulation.

SUMMARY OF THE INVENTION

According to a first aspect of the present invention, there is provided an external non-invasive fixator for fixing a fracture comprising proximal and distal portions for mounting on a limb either side of a fracture, each of the proximal and distal portions including a rigid member; and an articulation member connecting the proximal and distal portions, the articulation member comprising a universal joint for allowing relative movement between the proximal and distal portions, wherein the articulation member connects the rigid members.

By 'proximal' is meant the portion of the fixator for mounting nearest the body of a patient, while "distal" means the portion of the fixator for mounting furthest from the body of a patient.

The present invention allows for bone fragments to be maintained in position during healing by virtue of the rigid members and proximal and distal portions. The articulation member permits movement between the two portions of the fixator, such that the patient is able to flex a joint or move a limb in the vicinity of the fracture to alleviate fatigue and reduce stiffness while still retaining the fracture fragments in alignment. Further, the fixator is non-invasive and hence there is no risk of infection or complications of invasive surgery. Being non-invasive, the fixator can be placed in such a fashion that the plane of movement of the joint is in line with the plane of movement of articulating segment of the device, so minimising the chances of disturbing the position of fracture fragments when the joint is mobilised, improving patient comfort and healing. With invasive pin fixators such positioning is difficult to achieve because placement of the pins is constrained by the presence of the thumb, vital structures or other members of the limb.

The device of the invention is suitable for fixing a fracture. The term fracture includes a fracture of the long bones. In one embodiment, the fixator of the invention is used to treat long bone fractures. The device can be used during all stages of fixing the fracture, including for fracture reduction (moving the broken pieces of bone to normal configuration), fracture manipulation (moving fracture fragments) and treating fractures in such a fashion that the joint in proximity can be mobilised wile maintaining the fracture position immobilised.

In a preferred embodiment, the articulating member allows all-plane movement and distraction.

The universal joint may comprise a ball-and-socket type joint, or may comprise a combination of planar joints or hinges arranged in a suitable orientation to permit movement in all three planes. Any other suitable arrangement may also be used.

The articulation member may comprise a selectively lockable universal joint. That is, the universal joint(s) may be selectively restricted in at least one plane of movement, preferably two planes, and more preferably all three planes, together or separately. In an alternative embodiment, the articulation member may comprise a universal joint lockable in three planes and one or more lockable plane joints. This allows the articulation member to be restricted in movement to the plane of movement of the patient's joint; this permits trans-articular movement of the patient's limb. The joints may be lockable by means of a grub screw or similar arrangement. The joints at the level of the fracture and the joint line may be separately lockable.

In preferred embodiments, the articulation member comprises at least two universal joints, each joint articulating with a respective portion of the fixator, and preferably with a respective rigid member. This arrangement allows for a greater degree of available movement of the fixator when fitted, as well as a greater degree of possible alignment of the fixator during fitting, to conform to the shape of the patients limb. The proximal part of the articulation member is at the level of the fracture. The distal part of the articulation member is at the level of joint line which also allows movement in the joint's plane of motion. Preferably, the two universal joint are at a right angle to each other. The universal joints are preferably independently selectively lockable; in this way one joint may be left unlocked or locked in only one or two planes to permit movement of the limb, while the other joint may be locked in position to maintain a desired alignment of the proximal and distal portions of the fixator. The arrangement permits translation, distraction, and movement in all planes at the fracture site and/or at the level of joint line. A universal joint or combination joints may be provided at the level of the fracture and at the level of the joint line.

The articulation member may also comprise a hinge joint. In one preferred embodiment, the articulation member comprises a combination of two universal joints and a hinge joint and a distraction mechanism. Preferably, the two universal joint are at a right angle to each other. All joints may be selectively lockable. The provision of two universal joints with distraction mechanism allows for the fragment of a bone between the fracture site and joint (the broken piece) to be distracted/displaced in all three planes. This arrangement of the articulation member with selectively lockable joints allows for fracture pieces to be manipulated, reduced in position, immobilised at fracture site and yet allows mobilisation of the joint in single plane. Thus, the articulating member according to the invention allows for the hinge movement to be possible in all planes including movement along the axis of joint motion by virtue of selective locking capacity of two universal joints and the hinge joint.

Therefore, in a preferred embodiment, the articulating member allows all-plane movement and distraction.

The articulation member may be extendable, such that the length of the member may be adjusted. This may conveniently be provided by a telescopic portion of the member. The articulation member is preferably lockable such that the length is fixed when locked. The articulation member may be extended in use in order to provide for distraction of the fracture to assist healing. The articulation member may conveniently comprise a threaded extendable portion, such that the length may be adjusted in small increments relatively straightforwardly.

In preferred embodiments, the articulation member further comprises one or more measurement scales. Scales may be provided on the extendable portion, to measure the length of extension; or on one or more of the universal joints where present to measure the angle formed by the joints.

Preferably, the articulation member is not made of a coil arrangement which would offer resistance to restrict the movement of the joint.

The rigid members are preferably elongate, and preferably rigid rods. Conveniently the rods are formed of carbon fibre, although other materials may be used. Preferably, the rigid members extend substantially parallel with the long axis of the patient's limb.

One or preferably both of the proximal and distal portions are in the form of a cuff, which may be secured around a patient's limb. The cuff may be formed from rigid plastic or the like. Preferably, the cuff comprises an outer portion, of rigid material, and an inner portion, of resilient material. The resilient material may comprise an elastomeric material, such as neoprene or the like. Preferably, the resilient material may be waterproof; alternatively, or in addition, the resilient material may be breathable.

In another embodiment of the invention, the inner lining of the cuff is made of water proof and air tight bladder. The term bladder is used to define an inflatable chamber or vesicle that can be air filled or filled with liquid. The bladder may comprise a valve. The bladder may have interconnected chambers so that it can be inflated using a single valve. The multiple chambers allow the bladder to conform to the shape of the limb of the individual patient. This bladder system is made such that it may be adherent to overlying semi rigid plastic material.

The inner portion of the cuff preferably has a relatively high coefficient of friction, such that the cuff is securely retained on the patient's limb. The outer portion of the cuff preferably does not in use extend fully around the patient's limb; the inner portion preferably does so extend. This reduces the risk that the rigid outer portion of the cuff will constrict the limb thereby causing swelling and compartment syndrome, while the inner portion may be used to provide a secure mounting of the cuff on the limb.

The proximal portion of the fixator may comprise two or more joined cuffs; this allows the fixation points to be located along the limb, providing a more secure fixation. The cuffs may be joined with a stiffened member; for example, a plastic strip or tongue.

Preferably, the cuffs comprise portions for attaching to the rigid member. The attachment portions may comprise sleeves or the like through which the rigid member may pass. The attachment portions may further comprise means for fixing the rigid member into position; for example, grub screws or the like. These may be loosened to permit adjustment of the location of the rigid member with respect to the cuffs.

Preferably, the cuffs according to the invention are secured to the limb so that once they are secured, they do not rotate or move otherwise.

Preferably, one or more of the proximal and distal portions and the articulation portion, are radiolucent; preferably, all of the said portions are radiolucent.

The fixator may further comprise an external sheath for concealing the fixator. This improves the aesthetics of the device.

Preferably the fixator is adapted for use on a patient's arm; conveniently the fixator may be located in use with the rigid member on the opposite side of the arm from the patient's thumb (the ulnar side), that can not be done with conventional invasive external fixators.

According to a further aspect of the invention there is provided a fixator for an arm, the fixator comprising proximal and distal cuffs for mounting on an arm either side of a fracture, each of the cuffs including a rigid rod extending substantially parallel with the long axis of the patient's arm; and an articulation member connected to each of the rigid rods at respective first and second universal joints.

A further aspect of the invention provides a method of fixing a fracture in a patient's limb, the method comprising securing proximal and distal portions of a fixator on a limb either side of a fracture; and adjusting an articulation member comprising a universal joint connecting the proximal and distal portions to a desired position.

The invention also provides a method of treating a fracture, the method comprising securing a fixator to a limb having a fracture, the fixator comprising proximal and distal portions each including a rigid member; and an articulation member connecting the proximal and distal portions, the articulation member comprising a universal joint for allowing relative movement between the proximal and distal portions.

The fixator is particularly useful in first aid methods when access to a hospital is not available as it can be readily applied. Furthermore, the fixator allows access to skin at the fracture site where local treatment, such as cryotherapy, may be applied. This is particularly important in fractures where significant soft tissue swelling ensues, such as ankle fractures. The fixator also allows for soft tissue access and wound care in postoperative cases.

The fixator may also be used in veterinary surgery.

As described above, the fixator described herein is particularly suitable for fracture fixation. Furthermore, the fixator described herein may also be used for soft tissues corrections and treatment of deformities. The articulations may provide the means for repeated adjustments. This is normally done by serial plaster casting which is time consuming and uncomfortable for the patient. The use of the fixator provides the advantage that it can be adjusted and allows movement of the joint.

Furthermore, the fixator described herein may be used after surgical procedures, which may comprise procedures on the bone or soft tissues or combination of both. These procedures may be for emergency or elective surgery where a certain position of the limb is to be maintained with or without allowing movement across the adjacent joint.

In a further embodiment of the invention, the fixator may also be provided as a kit of parts for assembly.

BRIEF DESCRIPTION OF THE DRAWINGS

These and other aspects of the present invention will now be described by way of example only and without limitation with reference to the accompanying drawings in which.

DETAILED DESCRIPTION OF THE DRAWINGS

Figure 1:
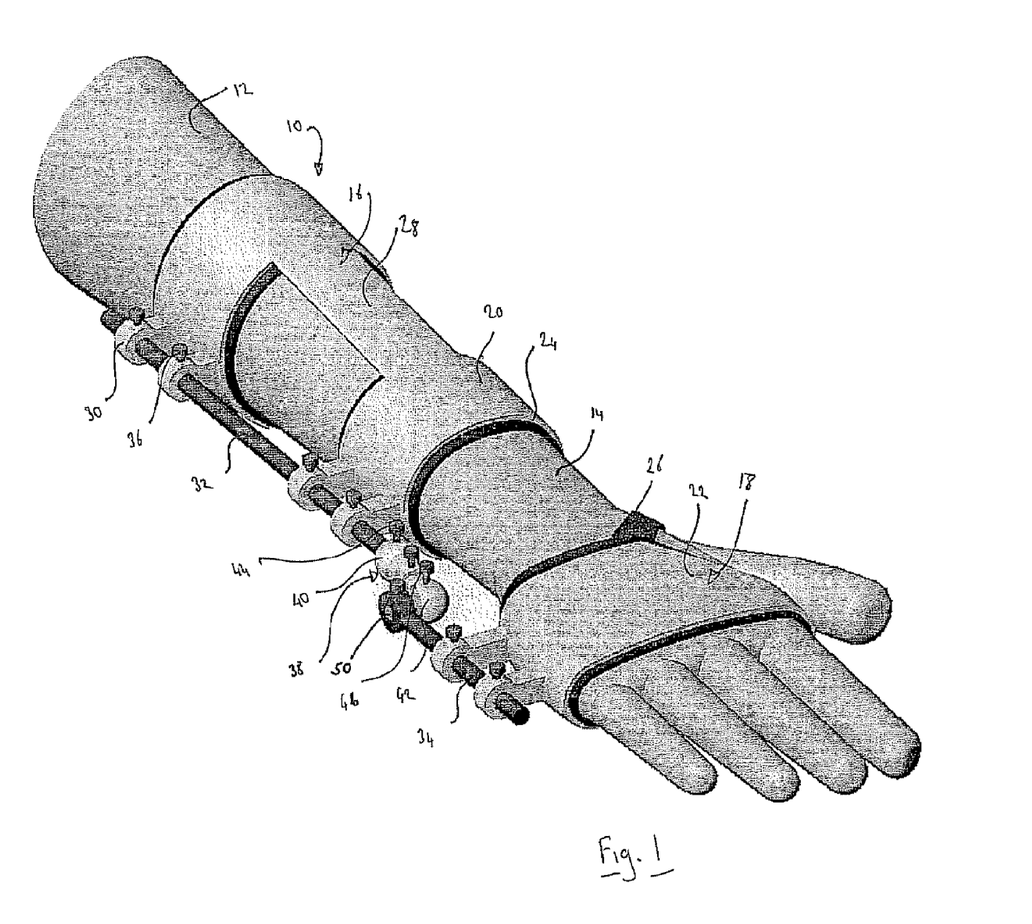
FIGS. 1 and 2 show perspective views of a fixator in accordance with an embodiment of the invention mounted on a patient's arm.
Figure 2:
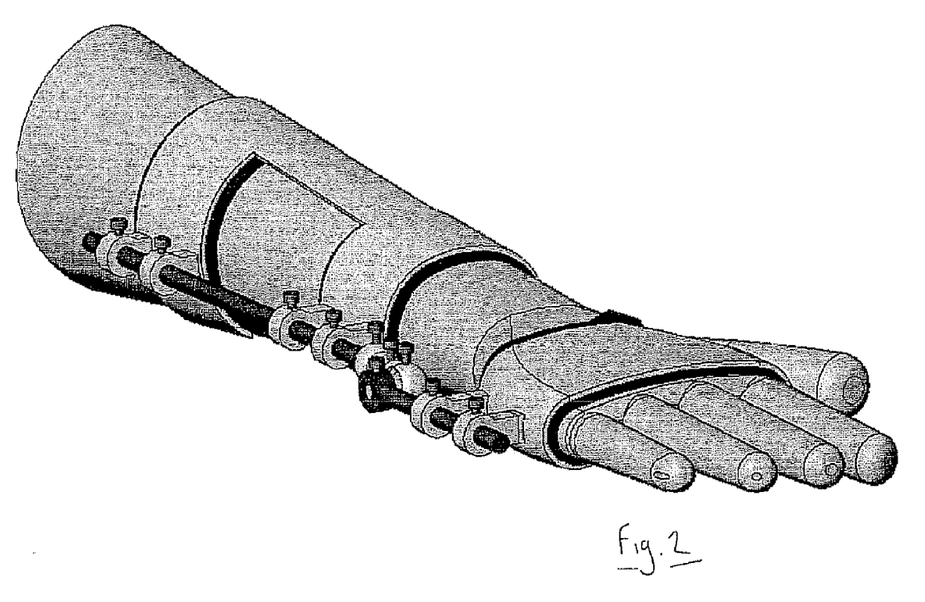
Figure 3:
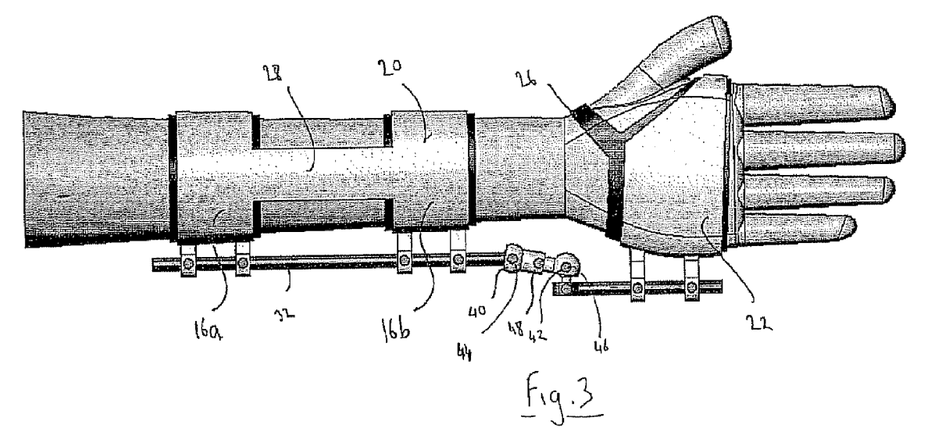
FIGS. 3, 4, and 5 show top, bottom, and side views respectively of the fixator of FIGS. 1 and 2.
Figure 4:
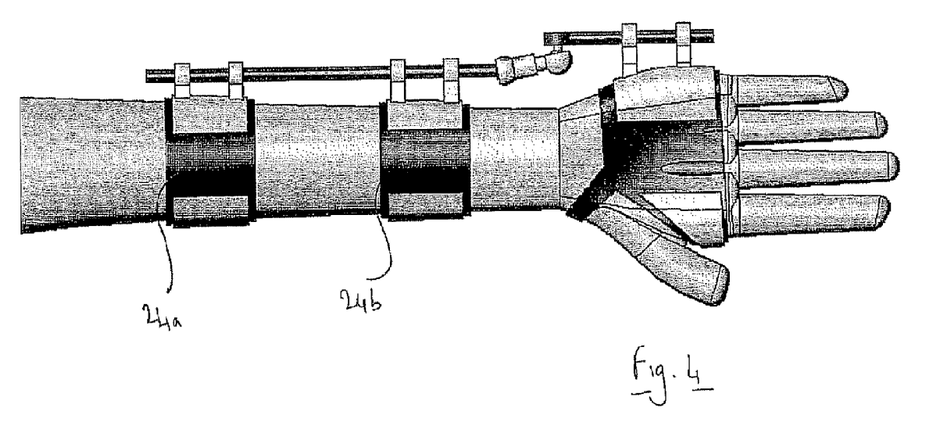
Figure 5:
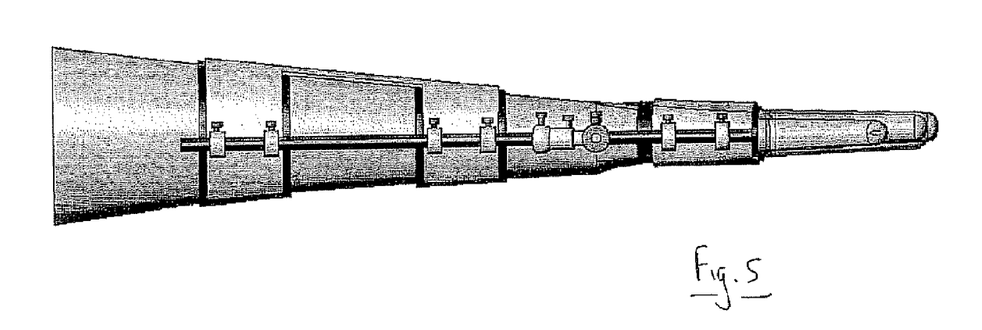

Referring to the Figures, a non-invasive external fixator 10 according to the present invention is shown mounted on an arm 12 of a patient. The arm 12 has a fracture 14 near the wrist.

The fixator 10 includes proximal 16 and distal 18 cuffs which are mounted either side of the fracture. Each cuff 16, 18 includes a rigid plastics outer shell 20, 22 which is open at the lower part thereof (seen best in FIG. 4), and a flexible elastomeric inner sleeve 24, 26 which encircles the patient's arm. The proximal cuff 16 is divided into two portions 16a, 16b which are connected by a connecting bar 28, and includes two inner sleeves 24a, 24b. The connecting bar 28 may be provided with an autograph plate. To fit the fixator onto the patient, the inner sleeves may be deformed to allow them to be passed over the patient's arm; the elastomeric nature of the inner sleeve will allow it to conform closely to the shape of the patient's arm. The outer shell may also similarly deform to allow the fixator to be secured to the patient.

Each cuff 16, 18 includes a number of rigid loops 30 through which pass proximal and distal carbon fibre rods 32, 34. The loops 30 are provided with grub screws 36 which may be tightened in order to retain the rigid rods within the loops.

The rods 32, 34 are joined by a connecting articulation piece 38. The articulation piece 38 has proximal and distal universal ball and socket joints 40, 42 which are connected to the respective proximal and distal rods. The proximal joint 40 is located at the level of the fracture 14, while the distal joint 42 is located at the level of the wrist joint. The ball and socket joints 40, 42 are at a right angle to each other and may be locked in position by means of grub screws 44, 46. The central portion of the articulation piece comprises a telescoping member 48, which may also be locked using a grub screw. The distal portion of the articulation piece 38 further comprises a lockable planar hinge joint 50, which permits rotation of the distal rod 34 in a single plane when the universal joint 42 is locked.

The articulation piece permits a range of useful movements of the fixator; the proximal and distal universal joints allow for the rods to be independently aligned and located relative to both the fracture and the limb joint, while the hinge joint 50 permits restricted movement of the limb joint when necessary. The universal joints may be fixed in position when the fracture is first set, or may be adjusted during healing to provide for translation, rotation, flexion, extension or mediolateral movement of the bones around the fracture site. Finally, the telescoping member permits longitudinal movement of the fixator to provide for distraction of the fracture. The articulation piece may include one or more graduated scales indicating the angle of adjustment of the universal joints, or the length of the telescoping member.

A further advantage of the fixator is that the rigid rods 32, 34 are located on the opposite side of the arm from the patient's thumb; this arrangement can be maintained even when the fracture is on the radial bone adjacent the thumb. In general the rods may be located at any convenient point on the fixator, thereby avoiding interference of the user's digits with correct positioning of the articulation piece.

The various components are radiolucent, so that they do not interfere with X-rays of the fracture. Also, by using suitable materials the fixator may be made light yet strong, as well as waterproof. In certain embodiments the fixator may include a cover to conceal the rods and other components for aesthetic reasons.

Although the described embodiment has been shown in use on an arm adjacent a wrist joint, it will be apparent that it may be used in other locations on the limb, such as adjacent the elbow, or on legs adjacent the knee or ankle. The shape and arrangement of the cuffs may be modified as appropriate. Further, although the articulating piece has been shown as essentially separate from the rods, in certain embodiments the universal joints and telescoping member may be integrated into the rigid rods.

Other modifications and variations will be apparent to the skilled person.

The invention claimed is:

1. An external non-invasive fixator for fixing a long bone fracture of a limb comprising proximal and distal portions for mounting on alongside of the long bone fracture, each of the proximal and distal portions including a rigid rod extending substantially parallel with a long axis of the limb, and an articulation member connecting the rigid rods that allows relative movement between the proximal and distal portions, the articulation member comprising a first universal joint that is arranged at a level of a joint line associated with a movable joint of the limb and a second universal joint that is arranged at a level of the long bone fracture, wherein the first and second universal joints are selectively lockable and unlockable to restrict and permit three-dimensional movement at each of the joint line and the long bone fracture.

2. The fixator of claim 1 wherein one or both of the proximal and distal portions are in the form of a cuff which may be secured around a patient's limb.

3. The fixator of claim 2 wherein the cuff comprises an outer portion of a rigid material and an inner portion of a resilient material.

4. The fixator of claim 3 wherein the resilient material comprises an elastomeric material.

5. The fixator of claim 3 wherein the outer portion of the cuff does not extend fully around the limb.

6. The fixator of claim 3 wherein the resilient material is waterproof.

7. The fixator of claim 2 wherein the cuff comprises an outer portion and an inner portion wherein the inner portion is made of one or more inflatable chambers.

8. The fixator of claim 1 wherein the length of the articulation member is adjustable.

9. The fixator of claim 8 wherein the articulation member comprises a telescopic portion.

10. The fixator of claim 8 wherein the articulation member is lockable such that the length is fixed when locked.

11. The fixator of claim 1 wherein the first and second universal joints are lockable in three planes, the fixator further comprising a lockable planar hinge joint coupled to the first universal joint that is configured to provide movement of the distal portion and the movable joint in a single plane.

12. The fixator of claim 11 wherein the first and second universal joints and the hinge joint are independently selectively lockable.

13. The fixator of claim 1, wherein the first and second universal joints comprise ball-and-socket type joints.

14. The fixator of claim 1 wherein the articulation member comprises one or more measurement scales.

15. The fixator of claim 1 wherein the proximal portion of the fixator comprises two or more joined cuffs.

16. The fixator of claim 1 wherein one or more of the proximal portion, the distal portion, and the articulation portion are radiolucent.

17. The fixator of claim 1 further comprising an external sheath for concealing the fixator.

18. The fixator of claim 1 wherein the limb is a patient's arm.

19. The fixator of claim 1, wherein the first universal joint and the second universal joint are configured at ninety degrees relative to each other.

20. A method of treating a long bone fracture of a limb, the method comprising:
    securing a fixator to the limb on alongside of the long bone fracture, the fixator comprising proximal and distal portions, each including a rigid rod extending substantially parallel with a long axis of the limb, and an articulation member connecting the rigid rods that allows relative movement between the proximal and distal portions, the articulation member comprising a first universal joint that is arranged at a level of a joint line associated with a movable joint of the limb and a second universal joint that is arranged at a level of the long bone fracture;
    articulating the second universal joint in three-dimensions to set the long bone fracture;
    locking the second universal joint; and
    selectively locking or unlocking the first universal joint to selectively restrict or permit movement at the joint line in three-dimensions.

21. The method of claim 20 further comprising adjusting at least one of the first universal joint, the second universal joint, and the hinge joint during healing of the long bone fracture to selectively provide for one or more of translation, rotation, flexion, extension, and medio-lateral movement of bones in the proximity of the long bone fracture.

22. The method of claim 20, further comprising selectively locking or unlocking a hinge joint coupled to the first universal joint to selectively restrict or permit movement of the distal portion and the movable joint in a single plane.

* * * * *